(12) United States Patent
Halsne

(10) Patent No.: US 7,653,435 B2
(45) Date of Patent: Jan. 26, 2010

(54) EXTERNAL DEFIBRILLATOR WITH MULTIPLE LANGUAGE PROMPTING

(75) Inventor: Eric Halsne, Seattle, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 352 days.

(21) Appl. No.: 11/572,824

(22) PCT Filed: Jul. 19, 2005

(86) PCT No.: PCT/IB2005/052419

§ 371 (c)(1),
(2), (4) Date: Jan. 29, 2007

(87) PCT Pub. No.: WO2006/016288

PCT Pub. Date: Feb. 16, 2006

(65) Prior Publication Data

US 2008/0097533 A1    Apr. 24, 2008

Related U.S. Application Data

(60) Provisional application No. 60/598,636, filed on Aug. 3, 2004.

(51) Int. Cl.
*A61N 1/39* (2006.01)
(52) U.S. Cl. .......................................... 607/5

(58) Field of Classification Search ................. 607/5–6, 607/115, 129
See application file for complete search history.

(56) References Cited

U.S. PATENT DOCUMENTS

| | | | |
|---|---|---|---|
| 6,597,949 B1 | 7/2003 | Dhurjaty | |
| 6,611,708 B1* | 8/2003 | Morgan et al. | 607/5 |
| 2002/0169482 A1 | 11/2002 | Servaas | |
| 2003/0055460 A1 | 3/2003 | Owen et al. | |
| 2003/0233129 A1* | 12/2003 | Matos | 607/5 |

\* cited by examiner

*Primary Examiner*—George R Evanisko
*Assistant Examiner*—Nicole F Lavert
(74) *Attorney, Agent, or Firm*—W. Brinton Yorks, Jr.

(57) ABSTRACT

A multilingual defibrillator is capable of concurrently providing audible prompts for the operation of the defibrillator in multiple languages. The defibrillator includes a memory for storing data files representative of audible prompts in a plurality of languages. A controller is coupled to the memory and configured to select data files of audible prompts in first and second languages and generate first electrical signals and second electrical signals representative of the audible prompts in the first and second languages, respectively. First and second audible sound generators are coupled to the controller to receive respective electrical signals and configured to generate audible output in response to the respective electrical signals.

11 Claims, 5 Drawing Sheets

EXTERNAL DEFIBRILLATOR WITH MULTIPLE LANGUAGE PROMPTING

CROSS REFERENCE TO RELATED APPLICATION

This application claims the benefit of U.S. provisional application Ser. No. 60/598,636 filed Aug. 3, 2004, which is incorporated herein.

The invention relates to an external defibrillator whose language of operation can be easily changed when the defibrillator is deployed for use.

Sudden cardiac arrest ("SCA") most often occurs without warning, striking people with no history of heart problems. It is estimated that more than 1000 people per day are victims of sudden cardiac arrest in the United States alone. SCA results when the electrical component of the heart no longer functions properly causing an abnormal sinus rhythm. One such abnormal sinus rhythm known as ventricular fibrillation ("VF") is caused by abnormal and very fast electrical activity in the heart. As a result, the heart fails to adequately pump blood through the body. VF may be treated by applying an electric shock to a patient's heart through the use of a defibrillator. Defibrillators include manual defibrillators, automatic or semi-automatic external defibrillators ("AEDs"), defibrillator/monitor combinations, advisory defibrillators and defibrillator trainers. The shock from the defibrillator clears the heart of abnormal electrical activity (in a process called "defibrillation") by producing a momentary asystole and an opportunity for the heart's natural pacemaker areas to restore normal rhythmic function. However, quick response after the onset of VF is critical because there is an increased likelihood that a patient will not be resuscitated or will suffer irreversible brain damage when the heart has not been pumping blood for more than 5 minutes.

Over the last several years defibrillators have become more portable and have begun moving into the hands of individuals who initially make contact with a person suffering from VF but have little or no formal medical training. As a result, equipment that was once available only in the hospital environment and operated by medically trained personnel is now being used in non-hospital environments by police officers, flight attendants and security guards, to name a few, as part of a first-line action in the administration of first aid. The benefit of making this equipment available is that it is more likely that a victim of SCA will receive the life-saving shock within the first few critical minutes of VF. Of course, with little or no medical training, the individuals who first make contact with a patient need to be instructed on the use of the defibrillator to deliver shock therapy. These defibrillators are often designed to operate nearly automatically and with little user intervention, often providing voice and text prompts to a medically untrained user on the operation of the defibrillator. Providing voice and text prompts for a user on the operation of a defibrillator reduces the amount of time necessary for the user to review protocols prior to deploying the defibrillator. Thus, a medically untrained individual first on the scene can nevertheless administer therapeutic shock to a patient in a short time.

As previously discussed, currently available external defibrillators often display instructions, status information or other information to assist the defibrillator operator on the operation of the defibrillator. Some external defibrillators announce such information audibly through a speaker, either in addition to displaying information or instead of displaying information. In areas where more than one language is commonly spoken, not necessarily with equal proficiency, there is a need to have a defibrillator that adapts the language of the prompts in response to the user's indication of language proficiency. This need is especially acute for defibrillators which are deployed in public areas, where there is no prior knowledge of which language a rescuer might speak. There are a number of locales where the need for a multilingual defibrillator is especially acute. The southern United States, for example, has a large number of people who speak exclusively English or exclusively Spanish. French Canada also has a population which may speak exclusively English or exclusively French. In Europe, many European languages coexist in a small area, increasing the likelihood of a rescuer who speaks a different language than the language set up on the defibrillator.

As a result, external defibrillators have been developed that can provide audible instructions and information on the operation of the defibrillator in different languages. These defibrillators are pre-programmed with audible instructions for more than one language from which audible instructions for one language are selected. Selection of the language in which the audible instructions and information are provided is typically made through button controls on the front panel of the defibrillator or through user responses to defibrillator prompts that are made during the operation of the defibrillator.

Although audible instructions on the operation of a defibrillator are available for different languages, the selection process for choosing which one of the languages to receive audible instructions can be distracting to a user, and also takes time to do. During a high stress rescue, any additional time or attention away from the task of applying rapid defibrillation to a patient only reduces the chance of success. Moreover, since the audible instructions are provided in only one language by the defibrillator, several rescuers having fluency in different languages will not be able to both benefit from the audible instructions provided by the defibrillator during administration of the therapy, thus precluding receipt of assistance from one or the other individual. Therefore, there is a need for a multilingual defibrillator providing audible instructions in more than one language during its operation.

The present invention is directed to a multilingual defibrillator capable of concurrently providing audible prompts for the operation of the defibrillator in multiple languages. In one aspect, the defibrillator includes a memory having stored therein data files representative of audible prompts in a plurality of languages. A controller also included in the defibrillator is coupled to the memory and configured to select data files of audible prompts in first and second languages and generate first electrical signals and second electrical signals representative of the audible prompts in the first and second languages, respectively. First and second audible sound generators are coupled to the controller to receive respective electrical signals and configured to generate audible output in response to the respective electrical signals.

Figure 1:
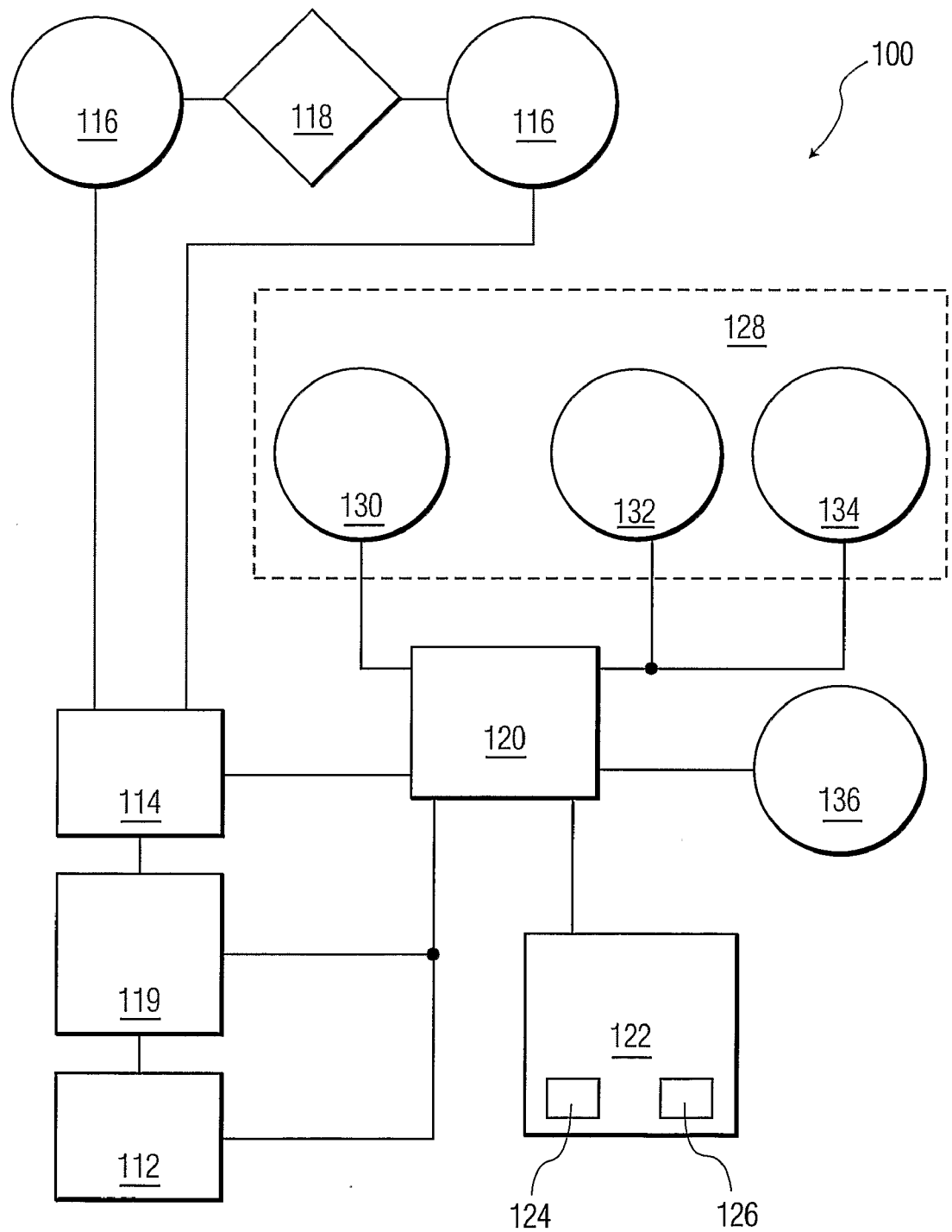
FIG. 1 is a diagrammatic representation of a defibrillator according to an embodiment of the present invention.

FIG. 1 is a block diagram of a defibrillator system 100 according to an embodiment of the present invention. The defibrillator system 100 includes an energy source 112 to provide voltage or current pulses. A controller 120 operates an energy delivery system 119 to selectively connect and disconnect energy source 112 to and from a pair of electrodes 116 connected to the defibrillator system 100 through an electrode interface 114. The electrodes 116 can be electrically attached to a patient 118 to provide electrotherapy to the patient. The defibrillator system 100 may be a manual defibrillator or AED. Alternatively, defibrillator system 100 may be a defibrillator trainer that simulates the behavior of a manual or automatic/semi-automatic defibrillator in use, in which case the electrode interface 114 and the energy delivery system 119 may be omitted.

In addition, controller 120 performs a protocol using information from an instruction generator 122. The instruction generator 122 includes a first memory 124 such as FLASH, EEPROM, ROM or RAM containing software code used to generate visual and audible instructions. The instruction generator 122 further includes a second memory 126 for storing software files for various languages in which audible instructions for the operation of the defibrillator 100 are available. In alternative embodiments, the instruction generator 122 may also include a gate array or other control logic. In other embodiments, the first and second memories 124 and 126 are included in a single memory device.

The instructions are delivered via an instruction output 128, which in the embodiment shown in FIG. 1 consists of a visual image generator 130, a first audible sound generator 132, and a second audible sound generator 134. The visual image generator 130 displays, among other things, visual commands to a user (either written or graphic representations). The visual image generator 130 may be, for example, a conventional liquid crystal display ("LCD"). Additionally, the first and second audible sound generators 132, 134 provide audible commands in first and second languages selected from the software files of the various language files stored in the second memory 126. Audible commands include verbal commands directing the user in the operation of the defibrillator 100. As will be explained in more detail below, the audible commands are provided in the first and second languages concurrently, one language broadcast from the first audible sound generator 132 and the other language broadcast from the second audible sound generator 134.

Activation of the visual image generator 130 and the first and second audible sound generators 132, 134 is controlled by the controller 120 in response to the information received from the instruction generator 122. The controller 120 and the instruction generator 122 determine the languages of the defibrillator instructions provided from the first and second audible sound generators 132, 134. Additionally, user input 136 may be provided to interact with the instruction generator 122 to select the desired languages of the defibrillator operating instructions. In the embodiment shown in FIG. 1, the user input 136 interacts with the instruction generator 122 via controller 120. In alternative embodiments the user input may interact directly with the instruction generator 122.

Figure 2:
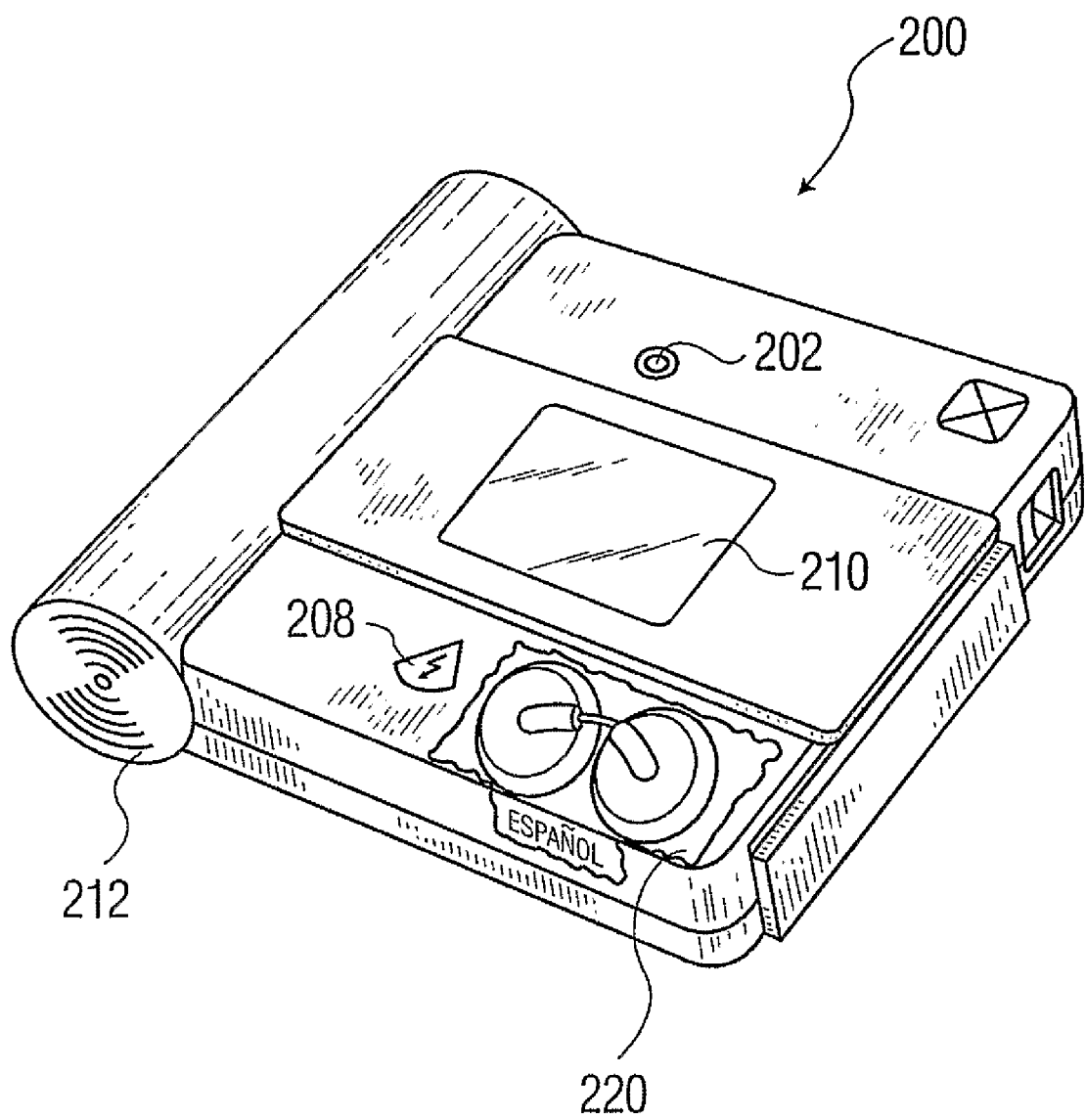
FIG. 2 is a top elevational view of a defibrillator according to an embodiment of the present invention.

In a preferred embodiment, the invention is incorporated into an AED 200 as shown in FIG. 2. An on/off power button 202 and a shock button 208 allow a user to power on and off the AED 200, and deliver an electrical shock from an energy source 112 (FIG. 1), respectively. The AED 200 also includes an LCD 210 on which visual information, such as visual commands on the operation of the AED 200, can be displayed for a user, and a speaker 212 from which audio output can be provided, such as audible commands from the instruction generator 122 (FIG. 1). A set of headphones 220 disposed in the AED 200 can be removed by a user to listen to audible commands on the operation of the AED 200 in a language different than the audible instruction s provided by the speaker 212. As a result, when audible commands on the operation of the AED 200 are provided, audible commands in a first language are provided by the speaker 212 and audible commands in a second language are provided by the headphones 220. The headphones 220 are distinctively marked as providing audible commands in the second language. For example, text written in the second language and clearly visible to a user can be used to label the headphones 220. Alternatively, other graphical means can be employed as well. In another embodiment, the bilingual availability can also be marked on the AED case enabling a second-language user to immediately apply the headphones 220 upon opening the case. In an alternative embodiment of the invention, audible information about the availability of audible commands in the second language through the headphones 220 can be provided in the first language through the speaker 212 during an initial phase of use of the AED 200.

By providing audible commands in a first language through the speaker 212, and audible commands in a second language through the headphones 220, a user who prefers to receive audible commands in the second language can deploy and employ the headphones 220, whereas a user who prefers to receive audible commands in the first language can ignore the headphones 220 and listen to the instructions provided by the speaker 212.

Figure 3:
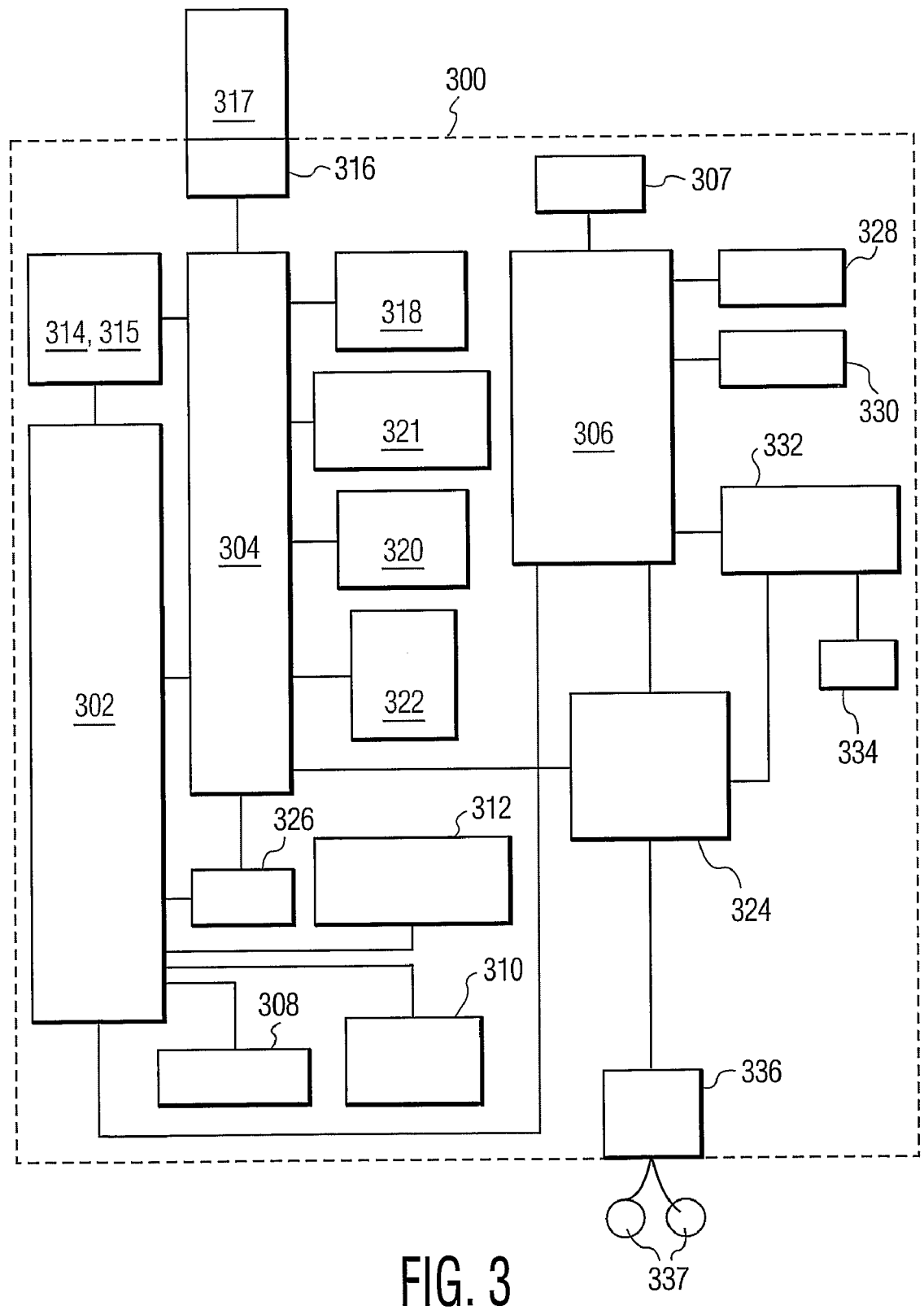
FIG. 3 is a functional block diagram of a portion of a defibrillator in which embodiments of the present invention can be implemented.

FIG. 3 is a schematic representation of some internal components of the AED 200. Control functions of the AED 200 are divided among a microprocessor unit (MPU) 302 and two custom gate arrays 304 and 306. For example, MPU 302 controls the functions of the shock button 208, as shown by block 326 in FIG. 3, while gate array 304 controls LCD 210, speaker 212, and headphones 220, as shown by blocks 318, 320, and 321 in FIG. 3. A first read-only memory ("ROM") 314 stores software instructions that are executed by the MPU 302. A second ROM 315 stores software files for various languages for which audible commands for the operation of the AED 200 are available. Further details regarding the remaining components of FIG. 3 may be found in U.S. Pat. No. 5,749,913, the disclosure of which is incorporated herein by reference.

In operation, the AED 200 can be pre-configured for languages through a setup program executed by the MPU 302. The setup process loads the software files for a default language and an alternate language into memory of the AED 200 so that audible commands for two different languages are available for listening during operation of the AED 200. At the time operation of the AED 200 begins, audible instructions in the default language prompting a user in the procedures to administer therapy using the AED 200 are provided by the speaker 212. In the event the headphones 220 are removed from the AED for use during this time, audible instructions in the alternative language will be made available through the headphones 220. Thus, as previously discussed, audible commands in one language are available through the speaker 212 and are available in another language through the headphones 220. In one embodiment, a sensor (not shown) is utilized to detect removal of the headphones 220 from the AED and initiate provision of audible instructions in the alternative language to the deployed headphones 220. As the operation of the AED 200 progresses, the appropriate instructions in the appropriate language are provided by the appropriate aural output device to instruct a user on carrying out a resuscitation procedure.

The selection of the default and alternative languages of the audible commands can be programmed at the time the AED 200 is deployed. The software files for audible instructions in several different languages can be stored in memory, thus, providing the option to select from several different languages to provide audible commands on the operation of the AED 200 form the speaker 212 and the headphones 220. The provision of audible commands in different languages is described in U.S. Pat. No. 6,154,673 to Morgan et al., which is incorporated herein by reference.

The default volume of the headphones 220 can be set high enough to be intelligible over the audible instructions from the speaker 212 which can be issued concurrently. Alternatively, the audible commands from the headphones 220 can be issued slightly out of phase with the audible commands from the speaker 212 such that both sets of prompts are heard clearly by a user wearing the headphones 220. Additionally, the audible instructions can be issued in parallel in both languages in order to advance the rescue at about the same rate. However, the AED may offset the aural prompts somewhat in order to reduce over-talk effects.

Figure 4:
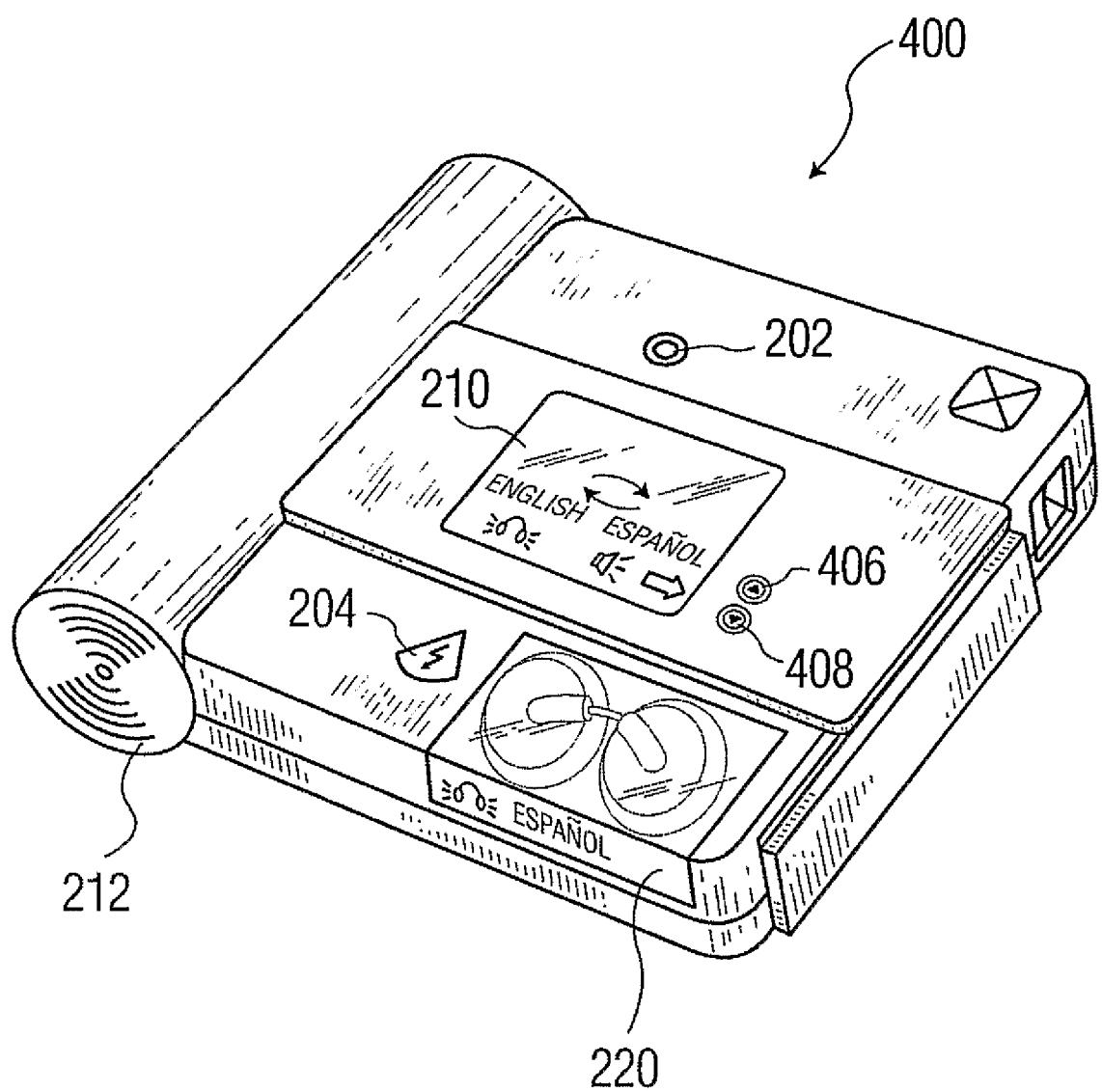
FIG. 4 is a top elevational view of a defibrillator according to an alternative embodiment of the present invention.

FIG. 4 illustrates an AED 400 according to an alternative embodiment of the present invention. The AED 400 is similar to the AED 200 of FIG. 2, and common reference numbers have been used to refer to common elements of the two AEDs. The AED 400, however, provides a user with the ability to switch the aural output devices from which the default and alternative languages are provided. Buttons 406 and 408 on the AED 400 can be used to swap the audible instructions provided by the speaker 212 and the headphones 220. When either button 406 or 408 is pressed, the MPU 302 (FIG. 3) senses the key press and generates command signals such that the gate array 304 switches the output of the speaker 212 and the headphones 220.

For example, as shown in FIG. 4, the aural output devices are the speaker 212 and the headphones 220 and the two languages are English and Spanish. As a default, audible commands on the operation of the AED 400 in English are provided from the speaker 212 and audible commands in Spanish are provided from the headphones 420. However, in the event that it is desirable for English audible commands to be provided from the headphones 220 and/or Spanish audible commands to be provided form the speaker 212, the buttons 406 or 408 can be depressed to swap the languages of the audible commands provided by the speaker 212 and the headphones 220. The depression of either button 406, 408 is detected and the MPU 302 commands the gate array 304 to switch the audible instructions of the speaker 212 and the headphones 220. The switch can be made while the AED 400 is operated. Thus, a Spanish language speaker who wishes to continue a rescue but without using the headphones 220 can press either buttons 406, 408 to switch Spanish language instructions to be provided from the speaker 212. Such a switching feature can also benefit a rescuer who is an English speaker in noisy environments where the ambient noise level is such that English instructions are difficult to hear from the speaker 212, such as on an aircraft in flight. Switching the output of the speaker 212 and the headphones 220 allows the user to have the English audible commands provided over the headphones 220 so that the instructions can be heard more easily in the presence of background noise.

In the embodiment shown in FIG. 4, switching of the aural output devices is made by using the buttons 406, 408. However, in alternative embodiments, the selector can be configured as a switch that is disposed elsewhere on the AED 400 or on the headphones 220. Additionally, the buttons 406, 408 can have additional functionality as well, such as adjusting the contrast of the LCD 210. The different functionality of the buttons 406, 408 can be distinguished by different methods, such as the time at which the buttons 406, 408 are pressed during the operation of the AED 400, or by the pattern of key presses.

Figure 5:
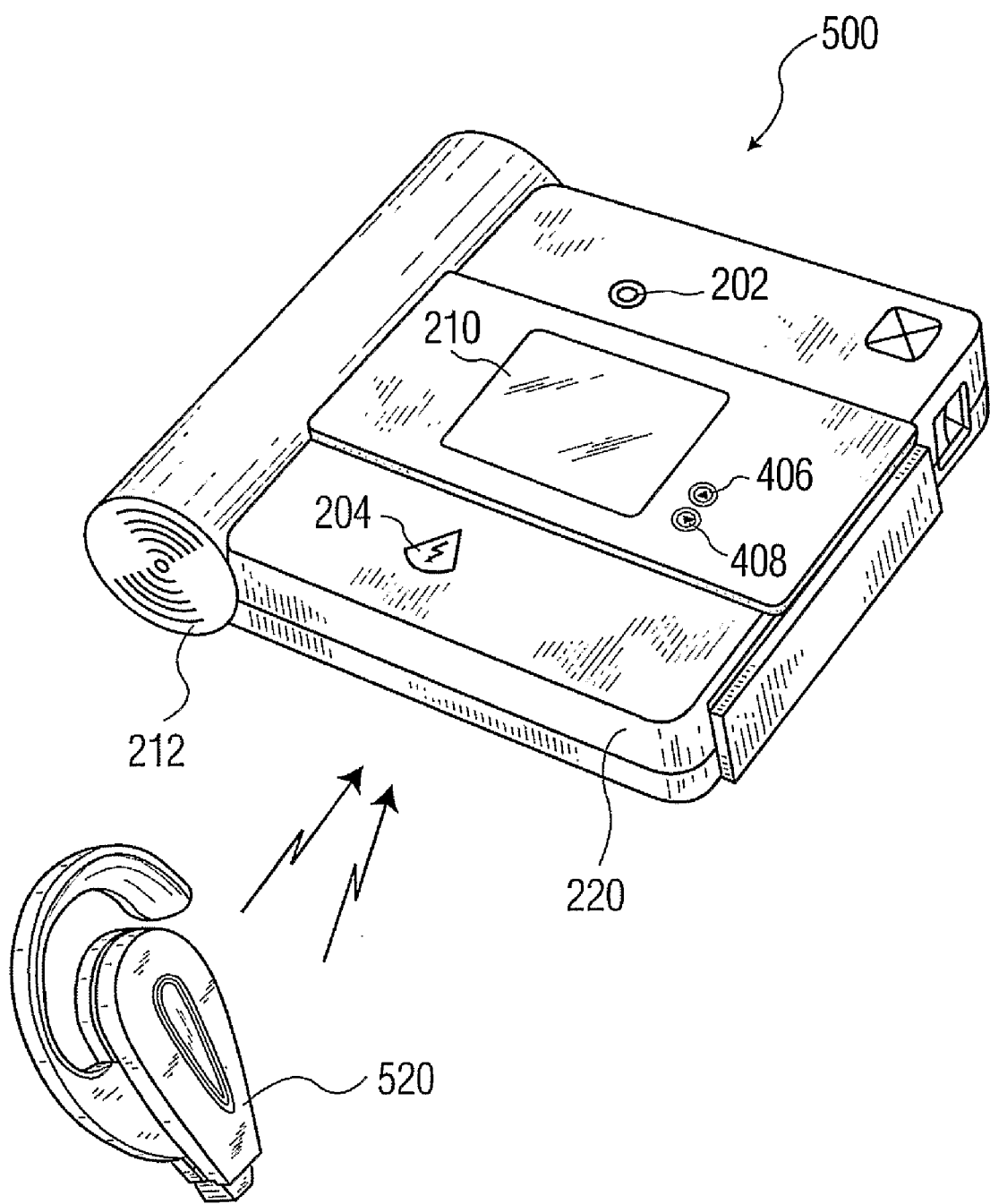
FIG. 5 is a top elevational view of a defibrillator according to an alternative embodiment of the present invention.

FIG. 5 illustrates an AED 500 according to an alternative embodiment of the present invention. The AED 500 is similar to the AEDs 200 and 400 of FIGS. 2 and 4, and common reference numbers have been used to refer to common elements of the AEDs. However, one of the aural output devices for the AED 500 includes a wireless earphone 520. The wireless earphone 520 eliminates the need for wires connecting the AED 500 and the wireless earphone 520. Although the us e of a wireless earphone 520 eliminates potentially interfering wires extending to the AED 500, a separate battery (not shown) will be needed to provide power. The battery for the wireless earphone 520 should be selected such that its useful and shelf lives match the life of the battery for the AED 500. Thus, both batteries can be replaced at the same interval. The use of a wireless earphone with a defibrillator is described in greater detail in copending U.S. patent application Ser. No. 60/545,820, filed on Feb. 19, 2004 and entitled METHOD AND APPARATUS FOR BROADCASTING AUDIBLE INFORMATION PROMPTS FROM AN EXTERNAL DEFIBRILLATOR, which is incorporated herein by reference.

As described therein, a wireless transmitter (not shown) included in the AED 500 will transmit signals to the wireless earphone 520 so that audible instructions can be provided therefrom. With reference to FIG. 1, either the first or second audible sound generators 132, 134 should be such a wireless transmitter. Additionally, with reference to FIG. 3, the block 321 should be modified to include or accommodate a wireless transmitter for transmitting the signals to the wireless earphone 520. Conventional wireless technology known in the art can be used for the wireless earphone 520 and the wireless transmitter in the AED 500.

Operation of the AED 500 is similar to that of AEDs 200 and 400, previously described. In activating the transmission of signals by the AED 500 so that audible commands are provided through the wireless earphone 520, the wireless earphone 520 can be attached to the AED 500 via a tether, the parting of which triggers the transmitter in the AED 500 to begin transmitting instructions to the wireless earphone 520 in the configured language. Alternatively, a sensor detecting the deployment of the wireless earphone 520 can be used as previously described with respect to the AED 200.

The invention claimed is:

1. An external defibrillator for delivering electrotherapy to a patient, comprising:
    a memory having data stored therein representative of audible information related to operation of the defibrillator in a first language and a second language;
    a controller coupled to the memory to retrieve the data representative of the audible information in the first language and the second language;
    a first aural output controller coupled to the controller to receive the data representative of the audible information in the first language from the controller and configured to generate first electrical signals corresponding to the audible information in the first language;
    a first aural output device coupled to the first aural output controller to generate audible output in response to the first electrical signals, the audible output corresponding to the audible information in the first language;
    a second-aural output controller coupled to the controller to receive the data representative of the audible information in the second language from the controller and configured to generate second electrical signals corresponding to the audible information in the second language; and a second aural output device coupled to the second aural output controller to generate audible output in response to the second electrical signals, the audible output corresponding to the audible information in the second language.

2. The external defibrillator of claim 1 wherein the first output device comprises a speaker and the second output device comprises a headphone.

3. The external defibrillator of claim 2 wherein the second aural output controller comprises a wireless earphone transmitter for transmitting signals corresponding to the second electrical signals and the headphone comprises a wireless earphone having a receiver for receiving the transmitted signals from the wireless earphone transmitter and configured to generate audible output in response to receiving the transmitted signals.

4. The external defibrillator of claim 2, further comprising a sensor coupled to the controller and located proximate to the headphone, the sensor detecting deployment of the headphone and generating an activation signal in response thereto, and the controller is further coupled to the sensor and configured to begin retrieval of the data representative of the audible information in the second language in response to receiving the activation signal.

5. The external defibrillator of claim 1 wherein the first and second aural output controllers comprise first and second aural output controllers configured to generate the first and second electrical signals concurrently.

6. The external defibrillator of claim 5 wherein the first and second aural output controllers are configured to generate the first and second electrical signals substantially simultaneously.

7. The external defibrillator of claim 1 wherein the first and second aural output controllers are configured to generate the second electrical signals following a time delay after the first electrical signals are generated.

8. The external defibrillator of claim 1 wherein the first and second aural output controllers comprise first and second aural output controllers configured to generate the first and second electrical signals in parallel.

9. The external defibrillator of claim 1 wherein the controller comprises a controller configured to switch the data provided to the first aural output controller and the data provided to the second aural output controller in response to receiving a user request.

10. The external defibrillator of claim 1 wherein the memory comprises a first memory in which the data representative of audible information in the first language are stored and further comprises a second memory in which the data representative of audible information in the second language are stored, the second memory removable from the external defibrillator.

11. The external defibrillator of claim 1, further comprising:
a pair of electrodes for delivering a therapeutic shock to a patient;
an energy source for providing electrical energy; and
an energy delivery system coupled to the energy source to receive the electrical energy, and further coupled to the pair of electrodes to deliver the electrical energy of the energy source as the therapeutic shock.

* * * * *